(12) United States Patent
Shuai et al.

(10) Patent No.: US 9,693,964 B2
(45) Date of Patent: Jul. 4, 2017

(54) HYDROXYPROPYL STARCH VACANT CAPSULES AND A PROCESS FOR PRODUCING THEM

(71) Applicant: Hunan Er-Kang Pharmaceutical Co., Ltd., Changsha (CN)

(72) Inventors: Fangwen Shuai, Changsha (CN); Xiangfeng Wang, Changsha (CN); Jiawei Zhang, Changsha (CN)

(73) Assignee: Hunan Er-Kang Pharmaceutical Co., Ltd. (CN)

( * ) Notice: Subject to any disclaimer, the term of this patent is extended or adjusted under 35 U.S.C. 154(b) by 4 days.

(21) Appl. No.: 14/482,363

(22) Filed: Sep. 10, 2014

(65) Prior Publication Data

US 2015/0297528 A1    Oct. 22, 2015

(30) Foreign Application Priority Data

Apr. 21, 2014    (CN) .......................... 2014 1 0159802

(51) Int. Cl.
*A61K 9/48* (2006.01)
*A23L 1/09* (2006.01)
*A61K 47/36* (2006.01)
*A23L 29/30* (2016.01)

(52) U.S. Cl.
CPC ............ *A61K 9/4816* (2013.01); *A23L 29/30* (2016.08); *A61K 47/36* (2013.01); *A23V 2002/00* (2013.01)

(58) Field of Classification Search
CPC ....... A23L 29/30; A61K 47/36; A61K 9/4816; A23V 2002/00
See application file for complete search history.

(56) References Cited

U.S. PATENT DOCUMENTS

| | | | | |
|---|---|---|---|---|
| 4,026,986 A * | 5/1977 | Christen | .................. | A61J 3/071 264/301 |
| 4,452,978 A * | 6/1984 | Eastman | ............. | A23L 1/05223 426/549 |
| 4,738,724 A | 4/1988 | Wittwer et al. | | |
| 6,641,837 B2 * | 11/2003 | Opheim | ................ | A61K 9/4816 424/451 |
| 2004/0105835 A1* | 6/2004 | Scott | .................... | A61K 9/4816 424/70.13 |
| 2006/0246127 A1 | 11/2006 | Freier | | |
| 2008/0138402 A1 | 6/2008 | Li et al. | | |
| 2011/0319503 A1 | 12/2011 | Muller et al. | | |
| 2013/0302309 A1 | 11/2013 | Yang | | |

FOREIGN PATENT DOCUMENTS

| | | | |
|---|---|---|---|
| CA | 2391963 A1 | | 5/2001 |
| CA | 2420600 A1 | | 3/2002 |
| CA | 2754382 A1 | | 9/2010 |
| CA | 2775227 A1 | | 3/2011 |
| CN | 1483393 A | | 3/2004 |
| CN | 1297601 C | | 1/2007 |
| CN | 1895234 A | | 1/2007 |
| CN | 1947709 A | | 4/2007 |
| CN | 1333006 C | * | 8/2007 |
| CN | 101182379 B | | 5/2008 |
| CN | 101245157 B | | 8/2008 |
| CN | 101273978 A | | 10/2008 |
| CN | 101338045 B | | 6/2010 |
| CN | 103070845 A | | 5/2013 |
| CN | 103638001 A | | 3/2014 |
| WO | 0103677 A1 | | 1/2001 |
| WO | 0192401 A2 | | 12/2001 |
| WO | 03039965 A1 | | 5/2003 |

OTHER PUBLICATIONS

Gooolge English translation of CN1333006C. Retrieved on Oct. 12, 2015.*
Chuenkamol et al (2007). "Characterization of low-substituted hydroxypropylated canna starch." Food Hydrocolloid, (21): 1123-1132.*
Extended European Search Report for Application No. EP14190233 dated Aug. 17, 2015.

\* cited by examiner

*Primary Examiner* — Anoop Singh
*Assistant Examiner* — Doan Phan
(74) *Attorney, Agent, or Firm* — Lerner, David, Littenberg, Krumholz & Mentlik, LLP

(57) ABSTRACT

This present invention discloses hydroxypropyl starch vacant capsules and a process for producing them, wherein said hydroxypropyl starch vacant capsules are made of hydroxypropyl starch and water and optional light-screening agent, colorant, aromatics, and flavoring agent through the processes of raw material mixup, gelatinization, stabilization, and capsule-forming. The hydroxypropyl starch capsules disclosed in this invention have such advantages as extensive source of raw material, high safety level, disintegrating property and friability over the products prepared through existing technologies.

7 Claims, No Drawings

HYDROXYPROPYL STARCH VACANT CAPSULES AND A PROCESS FOR PRODUCING THEM

CROSS REFERENCE TO RELATED APPLICATION

This application claims priority and benefits of Chinese Patent Application No. 201410159802.7, filed with State Intellectual Property Office on Apr. 21, 2014, the entire content of which is incorporated herein by reference.

FIELD OF INVENTION

This present invention relates to hydroxypropyl starch vacant capsules and a process for producing them, which falls into the pharmaceutical manufacturing industry.

BACKGROUND OF THE INVENTION

Capsule dosage as one of the most popular dosage forms, is widely used in pharmaceutical manufacturing industry, and particularly, vast majority of dietary supplements, such as the cod liver oil capsule and hard capsule of natural plant extracts, also take this dosage form.

Capsule dosage has the advantages of easy prescription, efficient development of process engineering and fast preparing process. Unlike the tablet dosage, the capsule content does not directly contact with the users' gustatory receptor, therefore, no flavoring agent or taste masking agent needs be considered. The filling and production process of capsule dosage is fairly simple—just need to fill the content inside the capsule shell and compress it into designed shape. As no similar study on the preparations and prescriptions of the tablet dosage is needed, the R&D and market-launch process of capsules dosages are much faster.

The most common raw material used to produce medicinal capsule is gelatin. This is mainly due to its properties of gelatinization, film-forming, and surface activity etc. Hard gelatin capsules prepared by dip molding method brings into full play its gelation and film-forming properties. The manufacturing process of this type of hard capsule includes the following steps: immersing the die pin in the hot gelatin solution, removing the die pin from the gelatin solution, cooling to make the gelatin adhered to the die pin solidified, drying and releasing from the die pin the capsule shell so formed.

As gelatin is derived from animal source, the gelatin capsule has potential safety hazard and is not welcomed by Islamic and Jewish believers. Additionally, people are showing increasingly more distrust of gelatin capsule due to the spread of BSE and the "Poison Capsule" scandal reported. In recent years, the research on the use of non-gelatin materials has gone up, which aims to avoid prion infection by abandoning the use of animal-source. This new type capsule, getting rid of animal-source gelatin, attempts to use natural material from plant, such as polysaccharides, vegetable gum, modified starch, substituted cellulose etc. Particularly, a number of trials have been done on modified cellulose, of which, the most successful case is the capsule made of HPMC, which demonstrates a number of advantages over gelatin capsules. However, the price of HPMC is much higher than gelatin.

Starch, as another kind of abundant natural polysaccharide, is a renewable resource and can be biodegraded. However, the successful use of starch has been impeded for some reasons. Firstly, the starch has poor mechanical properties and limited film-forming ability that makes it difficult for the viscosity or hardness to meet the requirement of a capsule's production; secondly, it can hardly meet the strict storage requirement of a capsule and has a relatively short shelf life due to its hygroscopicity. The only example in the industry (U.S. Pat. No. 4,738,724) is the starch capsule produced by injection molding. But the capsule so formed has much greater thickness and the capsule of different shape needs different customized mold filling and a closing device.

To solve this problem, the most frequently adopted practice is using starch as basic material and adding into it other materials to improve the overall mechanical properties; thus making it meet the requirement of capsule production. The most common materials added are: polysaccharide and plant gum, such as carrageenan, xanthan gum, gellan gum, guar gum, and furcelleran, etc, plus auxiliary plasticizers, adhesives and gel. For example:

Pat. No. CN103070845A discloses a starch vacant capsule and its preparation method, wherein the cross-linked high amylose is dissolved in water and stirred evenly into a 10~15% emulsion, and then heated at 50~55° C. for 15~25 minutes, followed by adding tributyl citrate, guar gum, span −80, and inulin. Well mix and keep heat isolated for 15-20 minutes, then defoam the solution and prepare starch vacant capsules by general dip molding method.

Pat. No. CN1297601C relates to a film-forming mixture composed of starch ether and a solidifying system, wherein the starch ether is hydroxypropylated starch or hydroxyethyl starch and the solidifying system is made of hydrocolloid or a combination of mixed hydrocolloids and cations. The said hydrocolloid is selected from polysaccharides. The content of hydroxypropyl starch ether is in the range of 88-98%; water, 2-12%; polysaccharide 0.01-10%; cations, 0.001-5%. Apply the conventional preparation method of gelatin capsule to prepare hard capsules.

Pat. No. CN1483393A discloses a starch vacant capsule and its preparation process, wherein the starch vacant capsule is composed of starch or starch derivatives, plasticizer, water, and other ingredients in the proportion of 25%-94.9%, 0.1%-30%, and 5%-20% respectively. The process is as follows: mix starch (or starch derivatives) and water as per the given proportion→heat the mixture to above 60° C. and mix uniformly→add plasticizer and mix evenly→allow to stay static and remove the bubbles→put the gel so formed into a insulation material trough→dip in the gel →dry →final product(capsules)

Pat. No. CN1333006C discloses a plant capsule made of mixed types of starches and the process for producing it, which uses 10 parts starch, 1-6 parts plasticizer, 0.15-2 parts gel agent, proper amount of surface active agent, and other auxiliary ingredients. The practical steps are as follows: mix the starch with water, and heat it to 60-95° C. for 15-60 minutes. Then add plasticizers, adhesives, gel agent and other auxiliary ingredients. Mix well and defoam, then prepare soft and hard capsules by common capsule forming equipment.

Pat. No. CN1895234A provides a plant vacant capsule and its preparation method, wherein said vacant capsule is made of natural plant material, and the components include 10 parts straight chain starch, 0.5 parts glycerol, and 6 parts purified water. The advantage of this invention lies in that it uses straight chain starch, glycerin, and water as the main raw material to prepare vacant capsules.

In addition, Pat. Nos. CN1947709A, CN103070845A, CN101182379B, CN101245157B, CN101273978A, and CN101338045B also released the plans to prepare plant capsules using plant-origin materials like starch and carrageenan gum.

However, there has not been a starch vacant capsule launched into the market up until now. The main reason is that the plant-based capsule products prepared so far has relatively poor stability and fails to match gelatin capsule in performance.

To solve the above mentioned problem, we have done research on both native and modified starch, during which we unexpectedly found that the gel made by gelatinizing hydroxypropyl starch (especially that with hydroxypropyl content at a certain range) at given temperature can stand stable for certain range of time at different temperature. The gel so formed can be made into capsules with the same quality as gelatin capsules by adding little or no plasticizers, adhesives and gel agent. No data or pertinent hint about this finding has been reported in existing technical literature.

SUMMARY OF THE INVENTION

The present invention aims to present a hydroxypropyl starch based vacant capsules and the process for producing them, wherein the hydroxypropyl starch vacant capsules can be used in the preparation of capsule dosages for pharmaceuticals, foods, and dietary supplements.

First, the hydroxypropyl starch based vacant capsule proposed in this invention is composed of adhesive, light-screening agent, colorant, aromatics, and flavoring agent.

Further, the formulation of the hydroxypropyl starch based vacant capsules described in this invention is as follows:

| | 80%~95%, |
| | 5%~15%, |
| | 0~5%, |
| | 0~3%, |
| | 0~2%, |
| | 0~4%, |
| | 0~5%. |

| Components | Weight percentage |
| --- | --- |
| hydroxypropyl starch | 80%~95%, |
| water | 5%~15%, |
| Adhesive | 0~5%, |
| Light-screening agent | 0~3%, |
| Colorant | 0~2%, |
| Aromatics | 0~4%, |
| Flavoring agent | 0~5% |

A hydroxypropyl starch vacant capsule, wherein the raw material hydroxypropyl starch is one or a combination of hydroxypropylated starches selected from the group of hydroxypropylated starches derived from mung beans, wheat, potato, cassava, soybean, or corn.

In order to improve the mechanical properties of the starch, small amount of adhesive can be selectively added. The adhesive added is one or a combination of adhesives selected from the group of glycerol, polyethylene glycol, triethyl citrate, tributyl citrate, stearic acid, and propylene glycol. The adhesive is an option, not a must.

In order to avoid the failure of some photosensitive drug, proper amount of light screening agent can be selectively added. The said light-screening agent can be titanium dioxide. According to practical requirements, the said colorant can be one or a combination of colorants selected from the group of Carmine Red, New Red, Amaranth, Allura Red, Erythrosine, Azorubine, Lemon Yellow, Sunset Yellow, Lactochrome, Canthaxanthin, Carotene, Chlorophyll, Acid Green BS, Brilliant Blue, Patent Blue V, Anthocyanin, Cacao Husk Pigment, Ferric Oxide, Caramel, Carbon Nanotubes, and Brilliant black.

In order to improve the drug compliance, aromatic could be used to better the special odor of some drugs. This is particularly suitable for children's medication. Depending on practical requirement and particular groups of users, the aromatic could be one or a combination of edible essence selected from the group of essence of different flavors such as apple, mint, orange, banana and pineapple.

In order to improve the drug taste, proper amount of flavoring agent could be added, which could be one or a combination of flavoring agents selected from the group of Sucrose, Mannitol, Xylitol, Sorbitol, Trehalose, Fructose, Maltose, Glucose, Steviosin, Sodium cyclamate, Acesulfame, Sucralose, and Aspartame.

Additionally, this invention brings forward a preparation process of hydroxypropyl starch vacant capsule, wherein the formulation are as follows: 85 parts raw material hydroxypropyl starch, 0-5 parts adhesive, 0-3 parts light-screening agent, 0-2 parts colorant, 0-4 parts aromatics, 0-5 parts flavoring agent, and proper amount of water.

The hydroxypropyl starch used in this process is one or a combination of hydroxypropylated starches selected from the group of hydroxypropylated starches derived from native mung bean starch, wheat, potato starch, cassava starch, soybean starch, or corn starch.

The content of hydroxypropyl starch used in this process is 2-7% by weight.

The adhesive used in this process is one or a combination of adhesives selected from the group of glycerol, polyethylene glycol, triethyl citrate, Tributyl Citrate, stearic acid, and propylene glycol.

The light-screening agent used in this process is titanium dioxide.

The colorant used in this process is one or a combination of colorants selected from the group of Carmine, New Red, Amaranth, Allura Red, Erythrosine, Azorubine, Lemon Yellow, Sunset Yellow, Lactochrome, Canthaxanthin, Carotene, Chlorophyll, Acid Green BS, Brilliant Blue, Patent Blue V, Anthocyanin, Cacao Husk Pigment, Ferric Oxide, Caramel, Carbon Nanotubes, and Brilliant black.

The aromatic used in this process is one or a combination of edible essence selected from the group of essence of different flavors such as apple, mint, orange, banana, and pineapple.

The flavoring agent used in this process is one or a combination of flavoring agents selected from Sucrose, Mannitol Xylitol, Sorbitol, Trehalose, Fructose, Maltose, Glucose, Steviosin, : Sodium cyclamate, Acesulfame, Sucralose, and Aspartame.

The present invention brought forward a preparation process of hydroxypropyl starch vacant capsules, wherein the hydroxypropyl starch vacant capsules are prepared through the following steps (a) to (f) using materials described above.

a) Preparation of Material A: Evenly mix adhesive and water in a container by the proportion of 1:1~2, and heat it to 60~80° C. Reserve for use. In the real production process, however, the adhesive is not a must but is added by proper amount only when necessary. If the adhesive is soluble in water, just mix it well with water by the proportion of 1:1. If it has relatively poor water solubility, then more water needs to be added to form suspension. Notably, the amount of water added here should not access 2 times the adhesive by weight, otherwise, it will affect the viscosity of the gel in the process D.

b) Preparation of Material B: Mix well the light-screening agent, colorant, flavoring agent, and water in a container by the proportion of 1:1~5. Reserve for use. In the real production process, however, the light-screening agent or colorant is not a must, nor is flavoring agent. They are just added by proper amount only when necessary. Depending on the solubility of light-screening agent, colorant, and flavoring agent, certain amount of water is added, but the amount added should not access 5 times the sum of the light-screening agent, colorant, and flavoring agent, otherwise it will affect the viscosity of the gel in the process E.

c) Preparation of Material C: Well mix aromatic and water in a container by the proportion of 1:1~3. Keep airtight and reserve for use. In the real production process, however, the aromatic is not a must but just added by proper amount only when necessary. Depending on the solubility of the aromatic, proper amount of water is added, but the amount added should not exceed 3 times the aromatic by weight, otherwise it will affect the viscosity of the gel in the process F.

d) Gelation: Put hydroxypropyl starch and water (at the proportion of 1:1~3) into the Gelation Tank, and heat it to 60~80° C. Adjust the pH to 7~9 with NaOH or phosphoric acid, and agitating the mixture for 1-2 hours at constant temperature to get Material D. And then add proper amount of Material A into Material D and mix well by agitating for 30 minutes to 1 hour at the temperature of 60~80° C. to form the Gel. The material D is a type of pasting liquid of the preliminarily gelatinized hydroxypropyl starch, which is then turned into gel after continuous gelatinization for another 30 minutes to 1 hour. The viscosity of the gel so formed is adjusted to the range of 400-1500 mPa·s by reducing or adding water.

e) Coloring: Add proper amount of Material B or the gel made through Gelation process into Material D, and then mix well.

f) Stabilizing and Capsule-forming: Put Material D or the post-coloring Gel into Gel Bucket A and B of the Automatic Vacant Capsule Machine. Maintain the temperature of the Buckets at 80~100° C. and allow to stand static for 1-2 hours. Then drop the temperature to 40~60° C. at the rate of 10° C./min and then follow either of the following two steps prior to processing it into vacant capsules by automatic capsule machine: 1) Allow to stand static for 1-2 hours; 2) Add material C, mix well, and then allow all to stand static for 1-2 hours. What needs to be addressed here is that the viscosity of the gel after standing static at 40~60° C. should be adjusted to 400~1500 mPa·s. In the preparation process of hydroxypropyl starch capsules, the patent applicant of this invention accidentally discovered that the mechanical properties of the Gel can be further improved after the following 2 phases of constant temperature: phase 1, stand static for 1-2 hours at constant temperature of 80~100° C.; phase 2, drop the phase 1 temperature to 40~60° C. at the rate of 10° C./min and allow to stand static for another 1-2 hours at this temperature. Additionally, the tailings remained in the capsule preparation process can be fully recycled for reuse by adding proper amount of water to form the gel with designed level of viscosity.

The hydroxypropyl starch vacant capsules produced by the said preparation process of hydroxypropyl starch vacant capsules can be used in the preparation of capsule dosages of pharmaceuticals, foods, and dietary supplements. In addition, the said preparation process of hydroxypropyl starch vacant capsules can also be used for producing other types of modified starch vacant capsules.

Compared with the technology existing before the date of filing, this invention has following prominent features and advantages.

(1) The hydroxypropyl starch vacant capsules are prepared using the main ingredient hydroxypropyl starch, and the optimal content of hydroxypropyl starch is 2%-7%. The Hydroxypropyl starch is obtained by simply hydroxypropylating the native starch.

(2) The capsules made from the gel formed from hydroxypropyl starch through the processes described in this invention—with little or no plasticizers, adhesives and gel agent added, can not only match gelatin capsules in properties, but also completely lift the security risk that may exist in gelatin.

(3) The tailings generated from this preparation process of hydroxypropyl starch vacant capsules can be reused by adding proper amount of water to form the gel with designed level of viscosity.

EMBODIMENTS

To further illustrate the practice of this invention, the following embodiments and examples are presented. It will be understood the examples are given for illustration purpose only and not by way of limitation.

Embodiment 1 a) Preparation of Material A: Evenly mix 4 kg glycerin and 4 kg water in a container and heat the mixture to 60~80° C. Reserve for use.

b) Preparation of Material B: Mix well 0.2 kg carmine, 1 k sucrose, and 1.2 kg water in a container at room temperature. Reserve for use.

c) Preparation of Material C: Mix well the 0.1 kg edible essence of orange flavor and 0.12 kg water in a container and keep it airtight. Reserve for use.

d) Gelation: Put 90 kg hydroxypropyl starch (with 2.3% hydroxypropyl content) and 160 kg water into the Gelation Tank, and heat to 60~80° C. Adjust the pH to 7~9 with NaOH or phosphoric acid and agitate the mixture for 2 hours at the same temperature to get Material D. Then add Material A into the Material D and well mix by agitating for 0.5 hour at the temperature of 70° C. to form the Gel.

e) Coloring: Add Material B or the gel formed in the Gelation process into Material D. Mix well.

f) Put the Gel formed in coloring process into Gel Bucket A and B in the Automatic Vacant Capsule Machine. Keep the Bucket temperature at 85° C. and allow the Gel stand static for 1.5 hour. Drop the temperature at the rate of 10° C./min until it hits 55° C. and allow the Gel stand static for another 1 hour at this point of temperature. Then add Material C, mix well, and keep static for one more hours. Use all-automatic capsule machine to process the Gel into capsules. The adhesive glycerol mentioned herein can be substituted by one or a combination of adhesives selected from the group of polyethylene glycol, triethyl citrate, Tributyl Citrate, stearic acid, and propylene glycol. The colorant carmine herein can be substituted by one or a combination of colorants selected from the group of New Red, Amaranth, Allura Red, Erythrosine, Azorubine, Lemon Yellow, Sunset Yellow, Lactochrome, Canthaxanthin, Carotene, Chlorophyll, Acid Green BS, Brilliant Blue, Patent Blue V, Anthocyanin, Cacao Husk Pigment, Ferric Oxide, Caramel, Carbon Nanotubes, and Brilliant black. The edible essence of orange flavor herein can be substituted by one a combination of edible essence of different flavors such as apple, mint, lemon, banana and pineapple.

Embodiment 2

Same as Example 1, except for the content of glycerol which is 1 kg in this Embodiment.

Embodiment 3

Same as Example 1, except for the content of hydroxypropyl starch which is 90 kg with 4.6%. Hydroxypropyl content.

Embodiment 4

Gelation: Put 95 kg hydroxypropyl starch (with 2.3% hydroxypropyl content) and 180 kg water into the Gelation Tank and heat to 70° C. and adjust the pH to 7.8. Agitate for 2 hours at a constant temperature of 70° C. to form the Gel.

Stabilizing and Capsule-Forming:

Put the Gel formed in the Coloring Process into Gel Bucket A and B of the Automatic Vacant Capsule Machine. Keep the Bucket temperature at 85° C. and allow the Gel stand static for 1.5 hours. Drop the temperature at the rate of 10° C./min until it hits 55° C. and allow the Gel stand static for another 2 hours at that temperature. Use all-automatic capsule machine to process the Gel into vacant capsules.

Embodiment 5

Gelation: Put 95 kg hydroxypropyl starch (with 2.3% hydroxypropyl content) and 180 kg water into the Gelation Tank; heat to 70° C. and adjust the pH to 7.8, then agitate for 2 hours at a constant temperature of 70° C. to form the Gel.

Stabilizing and Capsule-Forming:

Put the Gel obtained from coloring process into Gel Bucket A and B in the Automatic Vacant Capsule Machine. Keep the Bucket temperature at 95° C. and allow the Gel stand static for 1.5 hours. Drop the temperature at the rate of 10° C./min until it hits 45° C. and allow the Gel stay static for another 2 hours at that temperature. Use all-automatic capsule machine to process the Gel into capsules.

Contrasting Example 1

Gelation, Coloring: Put 95 kg hydroxypropyl starch (with hydroxypropyl content of 7.3%), 50 kg glycerol, and 180 kg water, 0.2 kg carmine, 1 kg sucrose, and 0.1 kg edible essence of orange flavor into the Gelation Tank. Heat to 70° C. and mix well by agitating for 2 hours at this temperature to form the Gel.

Stabilizing and Capsule-Forming:

Put the Gel formed in Coloring Process into Gel Bucket A and B in the Automatic Vacant Capsule Machine. Keep the Bucket temperature at 85° C. and allow to stand static for 1.5 hours at this temperature. Use all-automatic capsule machine to process the Gel into capsules.

Contrasting Example 2

Gelation, Coloring: Put 95 kg hydroxypropyl starch (with hydroxypropyl content of 7.3%), 50 kg, and 180 kg water, 0.2 kg carmine, 1 kg sucrose, and 0.1 kg edible essence of orange flavor into the Gelation Tank. Heat to 70° C. and mix well by agitating for 2 hours at this temperature to form the Gel.

Stabilizing and Capsule-Forming:

Put the Gel formed in the Coloring Process into Gel Bucket A and B in the Automatic Vacant Capsule Machine. Keep the Bucket temperature at 95° C. and allow to stand static for 1.5 hours at this temperature. Drop the temperature at the rate of 10° C./min until it hits 45° C. and allow the Gel stand static for another 2 hours at this temperature. Use all-automatic capsule machine to process the Gel into capsules.

Contrasting Example 3

All the processes involved are the same as those in Embodiment 1 except the temperature in the Gelation process, which is set at 50° C. in this example.

Contrasting Example 4

All the processes involved are the same as those in Embodiment 1 except the temperature in the Gelation process, which is set at 90° C. in this example.

Contrasting Example 5

All the processes involved are the same as those in Embodiment 1 except that the pH value of hydroxypropyl starch Gel is adjusted to 6.0 by phosphoric acid.

Contrasting Example 6

All the processes involved are the same as those in Embodiment 1 except that the pH value of hydroxypropyl starch Gel is adjusted to 10.0 by NaOH.

Contrasting Example 7

All the processes involved are the same as those in Embodiment 1 except that the Gel Bucket temperature is adjusted to 110° C. before the temperature drop.

Contrasting Example 8

All the processes involved are the same as those in Embodiment 1 except that the Gel Bucket temperature is adjusted to 60° C. before temperature drop.

Contrasting Example 9

The Gel viscosity is adjusted to 700 Pa·s in the Gelation process. In the Capsule-Forming process, the Gel viscosity is adjusted to 850 Pa·s after standing static at the temperature of 40~60° C.

Contrasting Example 10

The Gel viscosity is adjusted to 450 Pa·s in the Gelation process. In the Capsule-Forming process, the Gel viscosity is adjusted to 550 Pa·s after standing static at the temperature of 40~60° C. Take the capsules prepared by the processes of above Embodiments 1-5 and Contrasting Examples 1-2 and the gelatin capsules sold in the market. Test their tightness, friability, and disintegration time respectively according to the 2010 edition of "Chinese Pharmacopoeia".

TIGHTNESS: Test Method: Sample size: 10 capsules. Step 1: Gently pinch both ends of each capsule with thumb and index and twist to open. Step 2, Fill talcum powder in each capsule and jacket its cap and the body; allow the capsules to fall freely from 1 m height one by one to a 2 cm thick wooden board. Acceptance criterion: No adhesion, deformation or rupture should be found in Step 1, and no leakage or no more than one capsule leakage is allowed (if more than 1 capsule leaks, the test can be repeated for one time and the Acceptance Criterion must be met).

FRIABILITY: Test Method: Sample size: 50 capsules. Step 1 put the sample in the desiccator filled with saturated solution of magnesium nitrate, and place it under 25±1° C. constant temperature for 24 hours. Then take out the capsules and immediately place them in the glass tube (diameter: 24 mm, length: 200 mm) upright on a 2 cm thick wooden board. Allow a cylindrical weight (made of polytetrafluoroethylene, diameter: 22 mm, weight: 20 g±0.1 g) to fall freely from the top surface level of the glass tube. Acceptance criterion: No rupture should be found, or if there is rupture, it should be limited to less than 5 capsules.

DISINTEGRATION TIME: Test Method: Fill talcum powder in 6 capsules and follow the DISINTEGRATION TIME TEST METHOD under the category of Capsules (see Appendix A) to examine the disintegration time. Acceptance criterion: All the sample capsules tested must be completely disintegrated or dissolved within 30 minutes, if not, repeat the test for one more time.

Results : Tightness/particle friability/particle disintegration time/min

|  | Tightness/capsule | Friability/capsule | Disintegration time/min | Conformance to Requirements (Y/N) |
|---|---|---|---|---|
| Embodiment 1 | No leakage | Breakage (1 capsule) | 9 min 10 sec | Y |
| Embodiment 2 | No leakage | Breakage (1 capsule) | 9 min 19 sec | Y |
| Embodiment 3 | No leakage | Breakage (1 capsule) | 9 min 21 sec | Y |
| Embodiment 4 | No leakage | No breakage | 8 min 46 sec | Y |
| Embodiment 5 | No leakage | Breakage (1 capsule) | 9 min 22 sec | Y |
| Contrasting Example 1 | Leakage (1 capsule) | Breakage (4 capsules) | 17 min 46 sec | Y |
| Contrasting Example | Leakage (1 capsule) | Breakage (3 capsules) | 14分10秒 14 min 10 sec | Y |
| Contrasting Example 3 | No leakage slight coherence at the interface | Breakage (1 capsule) | 12 min 11 sec | N |
| Contrasting Example 4 | Leakage (1 capsule) | Breakage (4 capsules) | 16 min 27 sec | Y |
| Contrasting Example 5 | Leakage (2 capsule) | Breakage (3 capsules) | 11 min 08 sec | N |
| Contrasting Example 6 | No leakage, slight coherence at the interface | Breakage (1 capsule) | 12 min 14 sec | N |
| Contrasting Example 7 | Leakage (2 capsule) | Breakage (4 capsules) | 15 min 55 sec | N |
| Contrasting Example 8 | No leakage, slight coherence at the interface | Breakage (2 capsules) | 10 min 46 sec | N |
| Contrasting Example 9 | Leakage (2 capsule) | Breakage (5 capsules) | 17分36秒 17 min 36 sec | N |
| Contrasting Example 10 | No leakage, coherence at the interface | Breakage (1 capsule) | 10 min 58 sec | N |
| Gelatin capsules sold in the market | Leakage (1 capsule) | Breakage (1 capsule) | 10 min 44 sec | Y |

As the test result shows, the capsules produced according to the technical proposal described in this invention have certain quality advantages over the gelatin vacant capsules sold in the market, such as ideal friability, fast disintegration ability, and being free from leakage. Compared with the capsules prepared by the methods using the technical parameters beyond this invention, the capsules prepared using the technical parameters designed in this invention have better overall quality.

The invention claimed is:

1. A hydroxypropyl starch vacant capsule comprising:
   a hydroxypropyl starch, wherein the hydroxypropyl starch comprises a hydroxypropyl starch derived from a plant selected from the group consisting of native mung beans, wheat, potato, cassava, soybean, corn, and combinations thereof, wherein the hydroxypropyl starch is present in an amount of 80% to about 95% by weight and wherein the starch has a hydroxypropyl content of 2% to 7% by weight,
   water in an amount of from 5% to about 15% by weight,
   an adhesive selected from the group consisting of glycerol, polyethylene glycol, triethyl citrate, tributyl citrate, stearic acid, propylene glycol, and combinations thereof, wherein the adhesive is present in an amount up to 5% by weight, and
   at least one of a light-screening agent in amount up to 3% by weight, a colorant in an amount in an amount up to 2% by weight, an aromatic essence in an amount up to 4% by weight, and a flavoring agent in an amount of up 5% by weight;
   wherein the hydroxypropyl starch vacant capsule is made by a process that comprises:
   a) gelatinizing the hydroxypropyl starch comprising heating a mixture of the hydroxypropyl starch and water, in a ratio of from 1:1 to 1:3, to a temperature of 60-80° C., adjusting the pH to 7-9, agitating mixture for 1-2 hours at constant temperature, thus producing material D;
   b) mixing material D with water and the adhesive, for 0.5-1 hour at a temperature of 60-80° C., thus forming a gel;
   c) adjusting the gel viscosity of the gel to 400-1500 mPa·s;
   d) introducing the gel into gel buckets A and B of an automatic vacant capsule machine, while maintaining the temperature of the buckets at 80° C. to about 100° C. and allowing the gel in the buckets to stand static for 1-2 hours;
   e) lowering the temperature to 40° C. to about 60° C. at the rate of 10° C./min;
   f) allowing the gel in the buckets to stand static for 1-2 hours;
   g) adjusting the viscosity of the gel after standing static at a temperature of 40° C. to about 60° C. from 400 to about 1500 mPa·s; and
   h) forming the hydroxypropyl starch vacant capsule.

2. The hydroxypropyl starch vacant capsule of claim 1, wherein said lightening screening agent is titanium dioxide;
   said colorant is one or a combination of colorants selected from the group consisting of Carmine, New Red, Amaranth, Allura Red, Erythrosine, Azorubine, Lemon Yellow, Sunset Yellow, Lactochrome, Canthaxanthin, Chlorophyll, Acid Green BS, Brilliant Blue, Patent Blue V, Cacao Husk Pigment, Ferric Oxide, Caramel, Carbon Nanotubes, and Brilliant black;
   said aromatic essence is one or a combination of aromatics selected from the group consisting of apple, mint, orange, and pineapple; and
   said flavoring agent is one or a combination of flavoring agents selected from the group consisting of sucrose, mannitol, xylitol, sorbitol, trehalose, fructose, maltose, glucose, steviosin, sodium cyclamate, acesulfame, sucralose, and aspartame.

3. A process of preparing the hydroxypropyl starch vacant capsule of claim 1, the process comprising:
   a) gelatinizing the hydroxypropyl starch comprising heating a mixture of the hydroxypropyl starch and water, in a ratio of 1:1 to 1:3, to a temperature of 60-80° C., adjusting the pH to 7-9, agitating the mixture for 1-2 hours at constant temperature, thus producing material D;
   b) mixing material D with water and the adhesive, for 0.5-1 hour at a temperature of 60-80° C., thus forming a gel;
   c) adjusting the viscosity of the gel to 400-1500 mPa·s;
   d) introducing the gel into gel buckets A and B of an automatic vacant capsule machine, while maintaining the temperature of the buckets at 80° C. to about 100° C. and allowing the gel in the buckets to stand static for 1-2 hours;
   e) lowering the temperature of 40° C. to about 60° C. at the rate of 10° C./min;
   f) allowing the gel in the buckets to stand static for 1-2 hours;
   g) adjusting the viscosity of the gel after standing static at a temperature of 40° C. to about 60° C. from 400 to about 1500mPa·s; and
   h) forming the hydroxypropyl starch vacant capsule.

4. The process of claim 3, wherein said light-screening comprises titanium dioxide; said colorant comprises one or a combination of colorants selected from the group consisting of Carmine, New Red, Amaranth, Allura Red, Erythrosine, Azorubine, Lemon Yellow, Sunset Yellow, Lactochrome, Canthaxanthin, Carotene, Chlorophyll, Acid Green BS, Brilliant Blue, Patent Blue V, Anthocyanin, Cacao Husk Pigment, Ferric Oxide, Caramel, Carbon Nanotubes, and Brilliant black;
said aromatic essence comprises one or a combination of aromatics selected from the group of edible essences consisting of apple, mint, lemon, orange, banana and pineapple; and
said flavoring agent comprises one or a combination of flavoring agents selected from the group consisting of sucrose, mannitol, xylitol, sorbitol, trehalose, fructose, maltose, glucose, steviosin, sodium cyclamate, acesulfame, sucralose, and aspartame.

5. The hydroxypropyl starch vacant capsule of claim 1, wherein the ratio of the adhesive to the water that is added to material D is from 1:1 to 1:2.

6. The hydroxypropyl starch vacant capsule of claim 2, wherein f) further comprises adding to the gel a mixture of water and the aromatic essence.

7. The hydroxypropyl starch vacant capsule of claim 6, wherein the ratio of the aromatic essence to the water that is added to material D is from 1:1 to 1:3.

* * * * *